United States Patent [19]

Baillie

[11] Patent Number: 4,513,603

[45] Date of Patent: Apr. 30, 1985

[54] SYSTEM FOR MEASURING CRUSH PROPERTIES OF A CATALYST

[75] Inventor: Lloyd A. Baillie, Homewood, Ill.

[73] Assignee: Atlantic Richfield Company, Philadelphia, Pa.

[21] Appl. No.: 453,369

[22] Filed: Dec. 27, 1982

[51] Int. Cl.$^3$ ............................................. G01M 3/00
[52] U.S. Cl. ............................................. 73/37; 73/38
[58] Field of Search ..................... 73/37, 825, 38, 149, 73/798, 820

[56] References Cited

U.S. PATENT DOCUMENTS

| | | | |
|---|---|---|---|
| 2,345,935 | 4/1944 | Hassler | 73/38 |
| 2,821,680 | 1/1958 | Slusser et al. | 73/38 X |
| 3,199,341 | 8/1965 | Heuer et al. | 73/820 |
| 3,535,922 | 10/1970 | Pocock | 73/820 |
| 3,890,830 | 6/1975 | Dyck | 73/825 |

Primary Examiner—Howard A. Birmiel
Assistant Examiner—Hezron E. Williams
Attorney, Agent, or Firm—Donald L. Traut

[57] ABSTRACT

A system for measuring crush properties of a catalyst bed includes a catalyst bed container which includes at least one deformable wall around and adjacent to a catalyst bed. The catalyst bed container is enclosed within a pressure vessel. The pressure vessel is coupled to a pressure gauge and to a pump which acts to introduce measured quantities of an incompressible fluid such as water into the pressure vessel around the catalyst container. A pressure gauge is provided for measuring the pressure of the fluid within the pressure vessel. Two conduits extend from spaced positions within the catalyst vessel to the exterior of the pressure vessel, in order to create an air flow across a portion of the catalyst bed. Two spaced pressure taps also extend from locations within the catalyst vessel outside of the pressure vessel, and are coupled to a pressure sensor such as a manometer, for measuring the differential pressure between these two pressure taps. By measuring the volume of water introduced into the pressure vessel and the pressure drop across the catalyst bed within the catalyst vessel, each as a function of the pressure of the water in the pressure vessel, the crush properties and the flow resistance properties of the catalyst can be measured in a simple and efficient manner.

25 Claims, 5 Drawing Figures

`4,513,603`

SYSTEM FOR MEASURING CRUSH PROPERTIES OF A CATALYST

BACKGROUND OF THE INVENTION

This invention relates to systems for determining physical properties of a particulate bed such as a catalyst bed. More particularly, this invention relates to systems for determining load bearing and packing characteristics of fixed particulate beds such as those used in fixed bed reactors.

Efforts to determine packing properties or characteristics of catalysts have in the prior art often utilized systems which contained the catalyst in a rigid container. For example, one prior art approach has been to place a catalyst bed to be tested within a rigid cylinder, and then to apply forces to the upper surface of the catalyst bed by means of a piston which slides in the cylinder. An important drawback of this approach is that forces applied to the upper surface of the bed are not distributed uniformly throughout the bed. Instead, pressures in the bed are quite high near the piston, but decrease rapidly and non-uniformly with increasing distance from the piston.

Furthermore, many prior art efforts to determine crush properties of catalysts have been directed to measuring isolated physical characteristics such as crush strength and packing density. What really is of concern, however, to a catalyst user is a combination of properties, including packing, crush strength, differential pressure drop across a loaded bed, and flow characteristics of fluids through a packed bed.

These properties are not totally independent of one another. Packing influences the distribution of shearing and crushing forces experienced by individual catalyst particles within a loaded reactor. These forces cause attrition which results in a redistribution of packing and the forces resulting therefrom. If a significant increase in pressure drop across a catalyst bed occurs, the effectiveness of the loaded reactor to carry out catalyzed conversion processes can be decreased significantly. Crush strength of a catalyst can be important to whether a catalyst will pack in a commercially useful manner.

Since there has, up until now, been no single system of the type disclosed below capable of providing correlatable data between the physical properties of a particular catalyst and its ability to function in a loaded fixed bed, this invention fills a need not heretofore adequately satisfied. It is an object of this invention to provide a system, preferably a single apparatus, capable of providing correlatable data which can be used to predict the packing performance of a catalyst in a fixed bed reactor.

SUMMARY OF THE INVENTION

This invention relates to methods and devices for measuring the crush properties of a particulate bed.

According to one feature of this invention, an apparatus is provided which includes means for containing a particulate bed. This containing means includes a deformable wall around and adjacent to the bed. The containing means is enclosed inside a pressure vessel, such that an annular space is defined between the pressure vessel and the containing means. Means are provided for pressurizing a first fluid in the pressure vessel around the containing means and for measuring resulting volumetric changes in the containing means. In addition, means are provided for introducing a second fluid into the containing means at a first position in the bed, and for removing the second fluid from the containing means at a second position in the bed, separated from the first position such that the second fluid moves across a selected portion of the particulate bed. Moreover, means are provided for measuring the pressure differential between two spaced locations in the bed as an indication of the pressure gradient across the bed.

As will be described in detail below, the apparatus described above can be used to measure both volumetric changes and pressure gradient changes in the particulate bed as a function of the pressure to which the bed is subjected. In practice, these measurements have been found to be quite useful in predicting the packing and pressure gradient characteristics of fixed catalyst beds in a loaded catalytic reactor.

According to the method of this invention, an apparatus is used to obtain the volumetric and pressure gradient information described above. This method includes the steps of providing a particulate bed and an apparatus for measuring the crush properties of the bed. This apparatus comprises a container surrounding the bed and adapted to transmit pressures applied to the exterior of the container to the bed. In the preferred embodiments described below, the walls of this container are adapted to transmit externally applied pressures uniformly and in substantially undiminished form to at least a majority of the particulate bed contained therein. In addition, a pressure vessel is provided which surrounds the container. The method of this invention includes the step of pressurizing a first fluid in the pressure vessel between the pressure vessel and the container in order to apply variable compressive forces to the container and thereby to the bed itself. Both the volume of the bed and the pressure gradient of a second fluid across a portion of the bed are measured as a function of the pressure of the first fluid.

In the preferred embodiments described below, the volume of the bed as a function of the pressure of the first fluid is measured by measuring the quantity of the first fluid introduced into the pressure vessel. In this embodiment, the pressure gradient of the second fluid is measured by means of two spaced pressure taps which are coupled to a manometer. Furthermore, in these embodiments, the pressure taps are placed in a region of substantially uniform flow to reduce measurement artifacts.

The method and apparatus of this invention provide the important advantages of providing correlatable data on the bed. Both the volume of the bed and the pressure gradient across a portion of the bed can be monitored simultaneously as the pressures applied to the exterior of the bed are progressively increased. These correlatable measurements allow the maximum permissible solids pressure to be determined for any particular particulate bed, and they provide an excellent indication of the packing and pressure gradient characteristics that can be expected of a particulate bed in actual use.

The invention itself, together with further objects and attendant advantages, will best be understood by reference to the following detailed description, taken in conjunction with the accompanying drawings.

DETAILED DESCRIPTION OF THE PRESENTLY PREFERRED EMBODIMENTS

Figure 1:
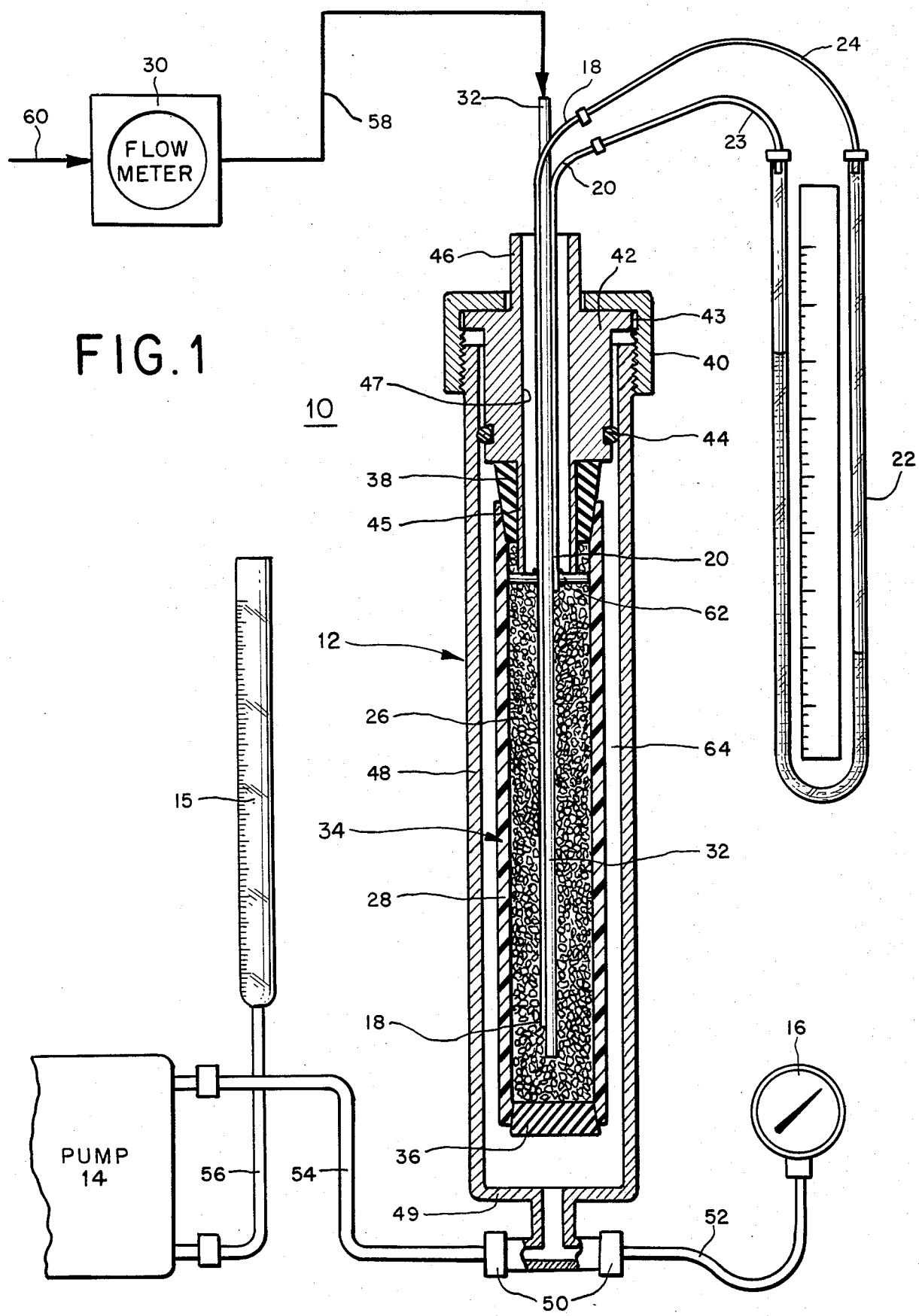
FIG. 1 is a partially schematic representation of a first presently preferred embodiment of the apparatus of this invention.
Figure 2:
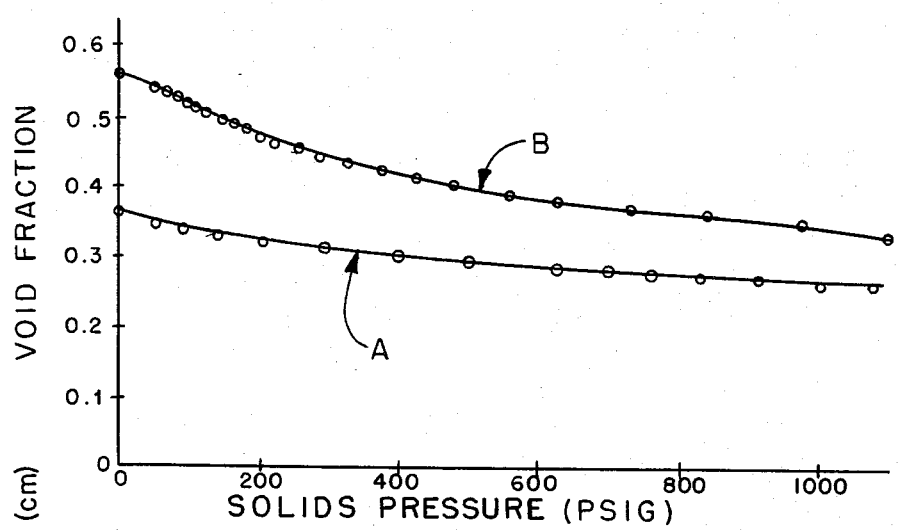
FIG. 2 is a graph showing the measured variation of void fraction as a function of solids pressure for two separate catalyst beds.
Figure 3:
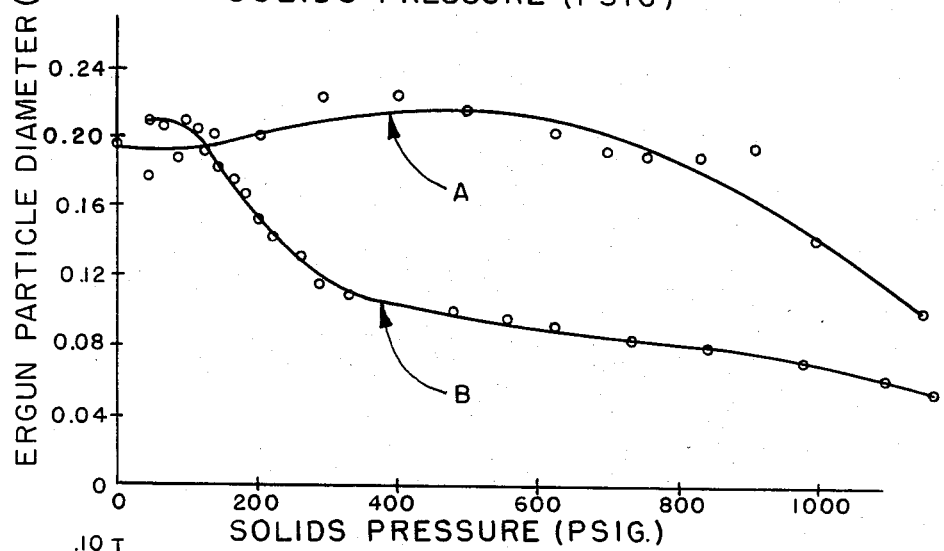
FIG. 3 is a graph showing the variation of Ergun particle diameter as a function of solids pressure for the two catalyst beds of FIG. 2.
Figure 4:
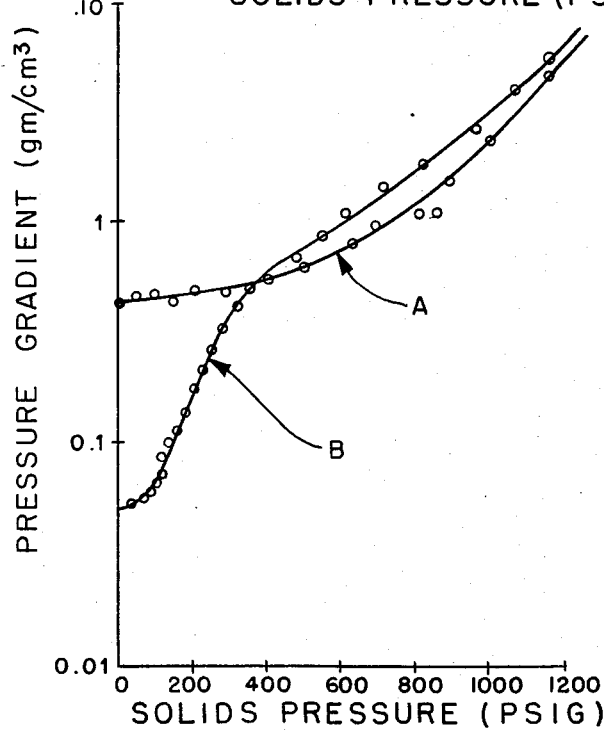
FIG. 4 is a graph showing the variation of pressure gradient as a function of solids pressure for the two catalyst beds of FIG. 2.

Turning now to the drawings, FIG. 1 shows a partially schematic representation of a presently preferred embodiment of the apparatus of this invention. FIGS. 2 through 4 are graphs showing the types of information that can be obtained by means of the apparatus and method of this invention.

As shown in FIG. 1, the presently preferred embodiment 10 of the apparatus of this invention includes a pressure chamber or vessel 12 which is generally cylindrical in shape, and which defines a vertical cylindrical wall 48 and a base 49. The pressure chamber 12 includes a threaded pressure cap 40 which is threadedly engaged at the upper end of the vertical cylindrical wall 48. In this preferred embodiment, the pressure chamber 12 defines an internal cylindrical volume approximately 2 inches in inside diameter and approximately 12 inches in length. The pressure chamber 12 is constructed to withstand internal hydraulic pressures in excess of 1200 pounds per square inch gauge (psig) without substantial expansion or leakage.

The interior of the pressure chamber 12 is connected to a hydraulic pump 14 by means of pressure fittings 50 and a conduit 54. In this preferred embodiment, the pump 14 is an electrically driven, hydraulic pump capable of generating hydraulic pressures in excess of 1200 psig. By way of example only, the pump marketed by Lapp Insulator Company, Inc. of Leroy, N.Y. as Model No. LS-10 is suitable for use in this embodiment.

The pump 14 acts to transfer a substantially incompressible fluid (such as water for example) from a calibrated burette 15 via the tubing 56 and 54, to the interior of the pressure chamber 12. Thus, by measuring the quantity of water removed from the burette 15, the quantity of water introduced into the pressure chamber 12 can be ascertained. In this preferred embodiment, the burette 15 has a capacity of 50 milliliters.

A pressure gauge 16 is connected to the pressure chamber 12 by means of tubing 52. In this preferred embodiment, the gauge 16 is a water-filled gauge which is capable of reading pressures up to 2000 psig. In order to minimize volumetric changes of the conduits 52, 54, 56 and the pressure vessel 12 as a function of hydraulic pressure, the conduits 52, 54 and the pressure chamber 12 are preferably formed of a material such as stainless steel tubing. Since tubing 56 is not subjected to high pressures, it can be formed of a plastic material such as Tygon.

In order to completely seal the interior of the pressure chamber 12, an interior cylindrical cap 42 is provided. This cap 42 defines an upper peripheral flange 43 which is interposed between the vertical cylindrical wall 48 and the threaded pressure cap 40 of the pressure chamber 12. The cylindrical cap 42 also defines means for retaining an O-ring seal 44. This O-ring seal 44 seals the annulus between the interior surface of the vertical cylindrical wall 48 and the cylindrical cap 42 in order to prevent the leakage of water out of the interior of the pressure chamber 12.

The interior cylindrical cap 42 also defines a lower sleeve 45. This lower sleeve 45 is in this embodiment approximately 1 inch in length, ⅜ of an inch in inside diameter and 7/16 of an inch in outside diameter. The lower sleeve 45 of this embodiment is formed of stainless steel tubing and is soldered in place on the lower surface of the cap 42. The lowermost end of the sleeve 45 is bent inwardly slightly. An upper sleeve 46 is also defined by the cap 42, and the upper sleeve 46 extends outwardly through an opening in the threaded pressure cap 40. The cylindrical cap 42 defines a bore 47 which extends completely through the upper sleeve 46, the cap 42, and the lower sleeve 45.

A catalyst vessel or container 34 is mounted on the lower sleeve 45 within the pressure chamber 12. This catalyst vessel 34 is in this embodiment made up of three parts: a cylindrical tube 28, an upper stopper 38, and a lower stopper 36. In this embodiment, the upper stopper 38 is glued to the lower sleeve 45, and both the upper stopper 38 and the lower stopper 36 are size 8 rubber stoppers which are concave at the small end. In this embodiment, the tube 28 is a plastic tube, which is preferably formed of Tygon, and which is 8¼ inches in length, 1.25 inches in inside diameter and 1.50 inches in outside diameter.

The catalyst vessel 34 serves to contain a catalyst charge or bed 26. This catalyst charge 26 is a particulate bed of the catalyst whose properties are to be measured. The catalyst vessel 34 serves to suspend the catalyst charge 26 inside the pressure vessel 12, while isolating the catalyst charge 26 from water pumped into the annular space 64 between the catalyst vessel 34 and the pressure chamber 12 by the pump 14.

The bore 47 defined by the cap 42 serves to provide access to the catalyst charge 26 to allow the pressure gradient across the catalyst charge 26 to be measured. In order to measure this gradient, a flow of a fluid is established across a portion of the catalyst charge 26. This fluid can be either a compressible fluid or an incompressible fluid, but the following discussion assumes that a compressible fluid such as air is used. In this embodiment, air is introduced into the catalyst charge 26 at a first location and withdrawing air from the catalyst charge at a second location, spaced from the first location. In practice, this can be done either by exhausting air from the catalyst charge at subatmospheric pressures or by introducing air into the catalyst charge at super-atmospheric pressures. In the preferred embodiment illustrated in FIG. 1, pressurized air is introduced into the catalyst charge 26 at a point near the lower stopper 36 by means of an air conduit 32. This air conduit 32 extends out of the pressure chamber 12 through the bore 47. The air conduit 32 is coupled to a flow meter 30 by means of tubing 58. The flow meter 30 is in turn coupled to a source of pressurized air (not shown) by means of tubing 60. Air which is introduced into the catalyst charge 26 via the air conduit 32 is allowed to vent from the catalyst vessel 34 through the bore 47 around the air conduit 32. The air conduit 32 is positioned with respect to the lowermost surface of the lower sleeve 45 by a crossbar 62 which is secured to the air conduit 32. In this preferred embodiment, the air conduit 32 is approximately 13¾ inches in length and is formed of a stainless steel, thin wall tube approximately 3/16 of an inch in diameter. The crossbar 62 is preferably formed of 16 gauge hypodermic tubing, and is welded to the air conduit 32. In this preferred embodiment, the air conduit 32 and the bore 47 cooperate to create an upward flow of air through the catalyst charge 26.

In order to measure the pressure gradient across the catalyst charge 26 induced by this upward flow of air, a differential pressure measuring system is provided. This pressure measuring system includes an upper pressure tap 20 and a lower pressure tap 18. Both of these upper and lower pressure taps 20, 18 are soldered in place on the air conduit 32. The lower pressure tap 18 is open at its lowermost end, which is situated near the lowermost end of the air conduit 32. Similarly, the upper pressure tap 20 is open at its lowermost end, which is situated near the lowermost end of the lower sleeve 45. In this preferred embodiment, both of the taps 18, 20 are formed of 16 gauge, stainless steel hypodermic tubing. The open ends of the two pressure taps 18, 20 are separated by about 6.7 inches. The exact placement of the open ends of the two pressure taps 18, 20 can be varied widely. In general, however, it is preferred to place these open ends such that the flow of fluid therebetween is uniform. If the lower tap 18 is placed too near the bottom of the container 34 or the upper tap 20 is placed too near the bore 47, unsatisfactory results may be obtained due to peculiar conditions that arise at either an inlet or an outlet. The upper ends of each of the pressure taps 18, 20 are connected by means of rubber tubing 23, 24 to respective ends of a glass tube manometer 22. In this embodiment, the manometer 22 is partially filled with methanol and it is formed of a 5/16 inch outside diameter glass tube.

The apparatus of FIG. 1 can be used to measure changes in both the volume and the pressure gradient across the catalyst charge 26, each as a function of the hydraulic pressure in the annular space 64 between the pressure chamber 12 and the catalyst vessel 34. In general, the apparatus of FIG. 1 can be used by first charging the catalyst vessel 34 with the catalyst charge 26 and then using the pump 14 to pressurize the pressure chamber 12. As pressure inside the pressure chamber 12 is gradually increased, the hydraulic pressure inside the pressure chamber 12 is measured by means of the gauge 16, and the volume of fluid introduced into the pressure chamber 12 is measured by means of the burette 15 as a function of the pressure indicated by the gauge 16. In addition, the flow rate of air through the air conduit 32 is measured with the flow meter 30, and the differential pressure between the upper and lower pressure taps 20, 18 is measured by means of the manometer 22 as a function of the pressure indicated by the gauge 16. In this way, the volume of the catalyst charge 26 and the pressure gradient across the catalyst charge 26 are measured, each as a function of pressure applied to the charge 26.

In greater detail, the apparatus of FIG. 1 can be used in the following manner. First, a known weight of a catalyst to be tested is placed in the catalyst vessel 34 by inverting the vessel 34, removing the lower stopper 36, and sprinkling the catalyst into the vessel 34. The catalyst vessel 34 is shaken until the maximum density of the catalyst charge 26 is obtained with the lower stopper 36 in place. Then the pressure chamber 12 is filled with water so that there are no air bubbles within the pressure chamber 12, and the catalyst vessel 34 is placed within the pressure chamber 12. Once all air has been removed between the pressure chamber 12 and the catalyst vessel 34, the theaded cap 40 is tightened to seal the pressure chamber 12. Water is then pumped in by means of the pump 14 until the pressure reading on the gauge 16 begins to rise. Then air flow through the flow meter 30 is regulated until the manometer 22 indicates one or two centimeters of methanol pressure differential. At this point, the flow as measured by the flow meter 30 is recorded. The pump 14 is then restarted and water is pumped at a rate of about 1 cc per minute from the burette 15 into the pressure chamber 12 until the pressure within the pressure chamber 12 reaches 1200 psig. The level of water in the burette 15 is recorded, as is the pressure indicated by the gauge 16, for every 2 cc of water pumped out of the burette 15. Furthermore, the flow rate indicated by the meter 30 and the manometer reading are recorded at the same intervals.

The measurements obtained in the manner described above can be used to generate graphs of the types shown in FIGS. 2, 3 and 4 by means of the following calculations.

The first step is to determine the particle density $D_P$ and the bed density $D_B$ for the catalyst to be tested. Particle density $D_P$ is calculated as the ratio of particle weight $W_P$ over particle volume $V_P$, where $W_P$ is dry weight and $V_P$ is measured by standard water displacement methods. Bed density $D_B$ is the maximum catalyst bed density, and is calculated as the ratio of the known weight of catalyst contained in a known bed volume $V_B$ at maximum density.

The next step is to measure the actual weight of the catalyst $W_B$ charged into the catalyst vessel 34. As explained above, the vessel 34 is then shaken to maximize the density of the catalyst bed, thereby causing it to equal $D_B$. The initial void fraction $e^o$, initial bed volume $V_B^o$ and initial void volume $V_V^o$ can be calculated by Equations 1, 2, and 3 as follows:

$$e^o = 1 - D_B/D_P, \qquad \text{(Eq. 1)}$$

$$V_B^o = (W_B/D_B); \qquad \text{(Eq. 2)}$$

$$V_V^o = V_B^o \times e^o. \qquad \text{(Eq. 3)}$$

Then the measured quantity of water pumped from the burette 15 into the pressure chamber 12 is used to determine changes in the void volume $V_V$, the bed volume $V_B$ and the void fraction $e$ as a function of pressure. The symbol $\Delta V$ will be used to designate the quantity of water removed from the burette 15 in pressurizing the chamber 12, corrected to account for any expansion of the chamber 12 or associated tubing 52, 54. The amount of correction to obtain $\Delta V$ will vary from embodiment to embodiment, and can be in part determined measured by pressurizing the chamber 12 without the catalyst vessel 34 in place. A second part of this correction is attributable to incomplete filling of the container 34. This second part of the correction is measured by noting the point at which the rate of change of water volume pumped from the burette with respect to pressure falls sharply. The rate of change of water volume with respect to pressure drops abruptly when the voids external to the catalyst bed have been eliminated by collapse of the container. This corresponds to the initial pressure change. It is assumed, for purposes of calculation, that the change of bed volume accompanying this initial pressure change is the same as the change of bed volume that results from the same pressure change after the voids external to the catalyst bed have been eliminated.

If it is assumed that $\Delta V$, the volume reduction of the catalyst bed, is entirely at the expense of the voids originally present, the void fraction e can be determined as a function of solids pressure by the following equation:

$$e = \frac{V_V^\circ - \Delta V}{V_B^\circ - \Delta V}. \quad \text{(Eq. 4)}$$

This assumption with regard the significance of $\Delta V$ is a good approximation provided $\Delta V$ has been corrected as described above and the pressure is not so great as to reduce the average particle size to the point where pore volume of the catalyst is changed substantially. Typically, this assumption is accurate for pressures up to at least 2000 psig.

FIG. 2 presents a graph of e versus solids pressure for two different catalysts as measured with the apparatus of FIG. 1. As used herein, the term "solids pressure" is used to indicate the pressure on the bed 26, and is equal to the pressure indicated by the gauge 16.

The pressure gradient across the catalyst bed can be determined as a function of solids pressure by first determining the area $A_B$ of the catalyst bed in a horizontal plane by the following equation:

$$A_B = \frac{V_B^\circ - \Delta V}{\text{Bed Length}} \quad \text{(Eq. 5)}$$

The air velocity V through the bed is the ratio of the measured volumetric flow rate indicated by the meter 30 divided by $A_B$ using consistent units of measure. The pressure gradient dp/dx between the two taps 18, 20 can be determined as the product of the manometer reading and the density of the manometer liquid, divided by the distance between the two taps.

From these parameters, the Ergun Diameter D can be determined from the Ergun Equation:

$$\frac{dp}{dx} = 150\mu V(1-e)^2/(gD^2e^3) + 1.75\rho V^2(1-e)/(gDe^3), \quad \text{(Eq. 6)}$$

where $\mu$ is the gas viscosity (poise), g is the gravitational acceleration (cm/sec$^2$), V is the superficial gas velocity (cm/sec), $\rho$ is the gas density (gm/cm$^3$), dp/dx is the vapor phase pressure gradient (gm/cm$^3$), and D is the Ergun Diameter (cm). The Ergun Equation is discussed in detail in a paper entitled "Fluid Flow Through Packed Columns" by Sabri Ergun (*Chemical Engineering Process*, Vol. 48, No. 3, pp. 89–94 (February, 1952)).

FIG. 3 presents the calculated Ergun Diameter D as a function of solids pressure for the two catalysts of FIG. 2.

Once the Ergun Diameter has been determined as a function of solids pressure, the Ergun Equation can be used to calculate pressure gradients for other fluids at the same or other gas velocities. FIG. 4 presents a graph of pressure gradient versus solids pressure at a flow rate of 1 ft/sec for the two catalysts of FIGS. 2 and 3.

The information of FIGS. 2, 3 and 4 can be used to assess the packing and flow restriction characteristics of a particulate bed as a function of solids pressure, and can be quite useful in evaluating the commercial potential of catalysts or in designing systems utilizing a particular catalyst. Catalyst void fraction, Ergun Diameter, and gas physical properties can be used to calculate vapor phase pressure gradients under actual reactor conditions.

In the calculations described above, the volume change required to force the catalyst vessel 34 tightly against the catalyst charge 26 is disregarded. It can be assumed that any superficial voids inside the catalyst vessel 34 have been eliminated by the time the hydraulic pressure reaches about 20 psig. The part of the incremental volume versus pressure curve between 0 and 20 psig is later filled in by extrapolation.

The apparatus of FIG. 1 provides the important advantage that it provides uniform solids pressure on the catalyst charge 26, which is otherwise difficult to achieve in rigid vessels, such as those formed by cylinders and pistons. In order to achieve the desired result of uniform solids pressure, it is important that the walls of the catalyst vessel 34 be chosen to have an appropriate rigidity. The distribution of stresses in particles is determined in part by the number of points in contact between a particle and neighboring surfaces. If a crush test in a test vessel is to measure the behavior of particles in a large vessel, it is important to ensure that particles near the wall of the test vessel are not subjected to more or less stress than are particles within the bed itself. Thus, if the walls of the catalyst vessel 34 are either too rigid or too conformable, inaccurate test results can be obtained.

For example, if the cylindrical wall of the catalyst vessel 34 were formed of a smooth metal with insufficient deformability, it would be expected that the number of points of contact between the wall and adjacent catalyst particles would be reduced, and that catalyst breakage near the wall would therefore be increased. On the other hand, experiments have shown that a rubber membrane substituted for the cylindrical wall of the catalyst vessel 34 conforms so closely to the catalyst particles at the surface that it reduces catalyst breakage.

For the foregoing reasons, it is preferred that the walls of the catalyst vessel 34 interact with the catalyst charge 26 in a way which is similar to the interaction between individual particles of the catalyst charge. It is possible to test for wall effects by performing duplicate crush tests in vessels of different diameters. Tests were performed in Tygon containers of 1.25 inch and 1.00 inch inside diameter. These tests gave essentially the same results, thereby suggesting that particles pressing against Tygon are stressed to about the same extent as particles surrounded by other particles of catalyst. This type of test can be repeated with other catalysts and with other types of catalyst vessel walls if there is a suspicion that wall effects are adversely influencing the test.

Figure 5:
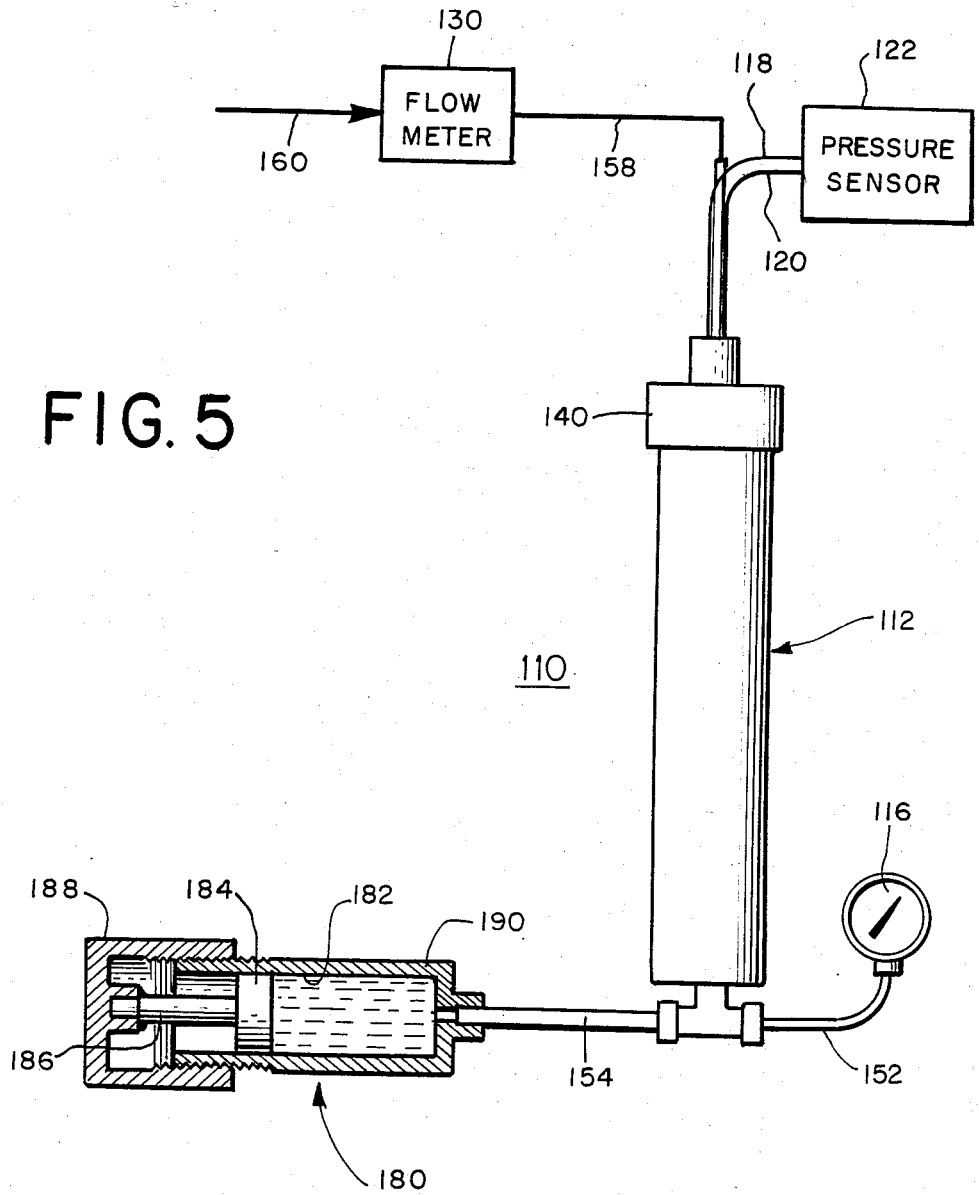
FIG. 5 is a schematic representation of a second presently preferred embodiment of the apparatus of this invention.

FIG. 5 shows a schematic representation of a second preferred embodiment 110 which is similar in many respects to the embodiment 10 of FIG. 1. In order to simplify the following explanation, comparable elements of FIGS. 5 and 1 are identified by reference numerals which are identical in the two right hand digits, and these comparable elements will not be further described here.

The embodiment of FIG. 5 differs from that of FIG. 1 most importantly in that a hydraulic cylinder 180 is substituted for the pump 14 and burette 15. The hydraulic cylinder 180 includes a cylinder block 190 which defines a bore 182. A piston 184 is slidingly positioned within the bore 182 to seal the block 190. This piston 184 is coupled by means of a piston rod 186 to a cap 188 which is threadedly coupled to the block 190.

Preferably, the hydraulic cylinder 180 is calibrated, such that the volume of the chamber bounded by the bore 182 and the piston 184 is a known function of the position of the cap 188 with respect to the block 190. The cylinder 180 is used by filling it with a fluid such as water, and then loading the catalyst vessel and the pressure chamber 112 as described above. Then the cap 188 is rotated to introduce known volumes of fluid into the chamber 112, and the pressure indicated by the gauge 116 is recorded as a function of volume. Data analysis can be performed as described above.

The apparatus and method of this invention are not limited to any particular means for pressurizing the fluid within the pressure chamber 12. Other pumps than those shown in FIGS. 1 and 5 may be used in alternate embodiments. Furthermore, it is not necessary to use a pump, per se, to introduce fluid into the pressure chamber 12, 112 in all embodiments. In one alternate embodiment, the volume of the pressure chamber 12, 112 is reduced in a known manner (as by tightening the cap 40, 140 for example) in order to raise the pressure in the pressure chamber 12, 112 while allowing reductions in the volume of the chamber 12, 112 to be measured.

As used herein, the term "pump" is used in a broad sense to encompass both the pump 14 of FIG. 1 and the cylinder 180 of FIG. 5, as well as other devices for pressurizing the pressure chamber 12, 112.

From the foregoing, it should be apparent that the present invention provides a system for measuring crush properties including volumetric changes and pressure gradient changes in a particulate bed as a function of the solids pressure within the bed itself. The system of this invention can be used to gain an understanding of the behavior of catalysts in actual operational conditions. It can be used to measure crush properties of a catalyst at a relatively low cost and in an efficient manner, and it can be used to provide a designer of a fixed bed catalyst system with information needed to optimize the catalyst system. This system has been found particularly effective in measuring the crush properties of fixed catalyst beds, and it has particular advantages in that application. However, this system can be modified to measure the crush properties of other fixed particulate beds, such as filter beds, as well.

Of course, it should be understood that various changes and modifications to the preferred embodiments disclosed above will be apparent to those skilled in the art. For example, the system of this invention can be embodied in apparatus which uses other means for measuring the volume of fluid introduced into the pressure vessel, or the pressure of the pressure vessel, or the rate of flow of air through the bed, or the pressure drop across the bed. In addition, other structures can be used for the catalyst vessel 34 and for the pressure chamber 12. It is therefore intended that the foregoing detailed description be regarded as illustrative rather than limiting, and that it be understood that it is the following claims, including all equivalents, which are intended to define the scope of this invention.

I claim:

1. An apparatus for measuring crush properties of a particulate bed comprising:

means for containing said particulate bed, said containing means comprising a deformable wall around and adjacent to said particulate bed;
 pressure vessel surrounding said containing means such that a space is defined between said pressure vessel and said containing means;
 means for pressurizing a first fluid, said first fluid pressure varying to at least that sufficient to crush said particulate bed disposed in said space;
 means for measuring the pressure of said first fluid;
 means for introducing a second fluid into said containing means at a first position in said particulate bed;
 means for removing said second fluid from said containing means at a second position in said particulate bed spaced apart from said first position, said removing means in fluid communication with said introducing means across at least a portion of said particulate bed;
 means for measuring pressure differential of said second fluid between two spaced locations in said particulate bed;
 means for measuring the volume of said first fluid introduced into said space as a function of said pressure of said first fluid;

2. The apparatus of claim 1 wherein said first fluid comprises an incompressible fluid.

3. The apparatus of claim 1 wherein said second fluid comprises a compressible fluid.

4. The apparatus of claim 1 further comprising means for measuring the rate of flow of said second fluid.

5. The apparatus of claim 1 wherein said deformable wall comprises a cylindrical plastic wall.

6. The apparatus of claim 1 wherein said differential pressure measuring means comprises a first and a second pressure tap situated at said two spaced locations in said particulate bed and a pressure sensor coupled to said first and second pressure taps to sense the pressure differential therebetween.

7. The apparatus of claim 1 wherein said pressurizing means comprises means for introducing measured quantities of said first fluid into said space.

8. The apparatus of claim 1 wherein said two spaced locations in said particulate bed are situated in a region of substantially uniform flow of said second fluid.

9. The apparatus of claim 6 wherein said first and second pressure taps in said particulate bed are situated in a region of substantially uniform flow of said second fluid.

10. The apparatus of claim 1 wherein said deformable wall transmits external pressures applied thereto by said first fluid to at least a substantial portion of said particulate bed.

11. A method for measuring crush properties of a particulate bed comprising the following steps:

varying the pressure on a first fluid disposed within a space between a particulate vessel surrounding said particulate bed and a pressure vessel surrounding said particulate vessel, said pressure varying from atmospheric to that sufficient to crush said particulate bed disposed in said space;
 transmitting a second fluid across a portion of said particulate bed;
 measuring the volume of said particulate bed as a function of said pressure of said first fluid; and
 measuring the pressure differential of said second fluid across a portion of said particulate bed as a function of the pressure of said first fluid, wherein said pressure differential measurement and said volume measurement are indicative of the crush properties of said particulate bed.

12. The method of claim 11 wherein said particulate vessel comprises a deformable cylindrical tube.

13. The method of claim 11 wherein said step of varying the pressure on said first fluid comprises introducing measured volumes of said first fluid into said space, and wherein said step of measuring the volume of said particulate bed comprises measuring the volume of said first fluid introduced into said space as a function of said pressure of said first fluid.

14. The method of claim 11 wherein said first fluid is comprises an incompressible fluid.

15. The method of claim 11 wherein said step of varying the pressure on said first fluid comprises progressively increasing said pressure on said first fluid.

16. The method of claim 11 wherein the step of transmitting said second fluid comprises:
introducing said second fluid into said particulate vessel at a first position in said particulate bed;
removing said second fluid from said particulate vessel at a second position in said particulate bed;
and the step of measuring the pressure differential comprises:
measuring said pressure differential of said second fluid between two spaced locations within said particulate bed; and
measuring the rate of flow of said second fluid between said first and second positions within said particulate bed.

17. The method of claim 16 wherein said second fluid comprises a compressible fluid.

18. The method of claim 16 wherein said two spaced locations in said particulate bed are situated in a region of substantially uniform flow of said second fluid.

19. The method of claim 11 wherein said particulate vessel transmits external pressures applied thereto by said first fluid to at least a substantial portion of said particulate bed.

20. The method of claim 11 comprising substituting said pressure differential and said flow rate of said second fluid into a formula comprising $$\frac{dp}{dx} = 150\mu V(1-e)^2/(gD^2e^3) + 1.75\rho V^2(1-e)/(gDe^3),$$

wherein D is indicative of pressure gradients to be produced by said particulate bed in use with fluids other than said second fluid.

21. An apparatus for measuring crush properties of a particulate bed comprising:
pressure vessel;
particulate vessel situated within said pressure vessel, said particulate vessel comprising a deformable wall adapted to transmit external pressures applied thereto by a substantially incompressible first fluid to the interior of said particulate vessel;
pump coupled to said pressure vessel for introducing said first fluid into the space between said pressure vessel and said particulate vessel, and pressurizing said first fluid to that sufficient to crush said particulate bed;
pressure gauge positioned to sense the pressure of said first fluid;
means for measuring the volume of said first fluid introduced by said pump into said space as a function of said pressure of said first fluid;
first tube extending from the exterior of said pressure vessel to a first location within said particulate vessel;
second tube extending from the exterior of said pressure vessel to a second location within said particulate vessel spaced apart from said first location;
means for establishing a pressure differential between said first and second tubes and for introducing a second fluid into said first tube in order to cause said second fluid to flow between said first and second locations;
first and second pressure sensor conduits extending from the exterior of said pressure vessel to second fluid pressure sensing points within said particulate vessel;
means for measuring the pressure differential between said first and second sensor conduits; and
means for sealing said particulate vessel around said first and second tubes and said first and second conduits to substantially exclude said first fluid from the interior of said particulate vessel.

22. The apparatus of claim 21 wherein at least a portion of said deformable wall of said particulate vessel is defined by a cylindrical plastic tube which operates to transmit pressures applied by said first fluid to the exterior of said plastic tube substantially uniformly to at least a substantial portion of said particulate bed contained in said particulate vessel.

23. The apparatus of claim 21 further comprising means for measuring the flow rate of said second fluid between said first and second tubes.

24. The apparatus of claim 21 wherein said first and second tubes are disposed concentrically and said first tube protrudes further into said particulate vessel than said second tube.

25. The apparatus of claim 24 wherein said first and second sensor conduits are mounted on the exterior of the one of said first and second tubes, and wherein said second fluid pressure sensing points are situated in a region of substantially uniform flow of said second fluid.

* * * * *